United States Patent [19]

Welstead, Jr.

[11] 4,324,791
[45] Apr. 13, 1982

[54] HETEROCYCLIC ANTIDIARRHEAL COMPOSITIONS & METHODS OF USE

[75] Inventor: William J. Welstead, Jr., Richmond, Va.

[73] Assignee: A. H. Robins Company, Inc., Richmond, Va.

[21] Appl. No.: 930,124

[22] Filed: Aug. 1, 1978

Related U.S. Application Data

[63] Continuation-in-part of Ser. No. 796,264, May 12, 1977, Pat. No. 4,120,969, which is a continuation-in-part of Ser. No. 615,952, Sep. 23, 1975, abandoned, which is a continuation-in-part of Ser. No. 541,684, Jan. 16, 1975, abandoned.

[51] Int. Cl.$^3$ .................................... A61K 31/445
[52] U.S. Cl. .................................... 424/267
[58] Field of Search .................................... 424/267

[56] References Cited

U.S. PATENT DOCUMENTS 3,192,230  6/1965  Lunsford et al. ............. 260/293.71

Primary Examiner—Stanley J. Friedman

[57] ABSTRACT

1-R-4-(omega-substituted alkyl)-3,3-diphenyl-2-pyrrolidinones of the formula

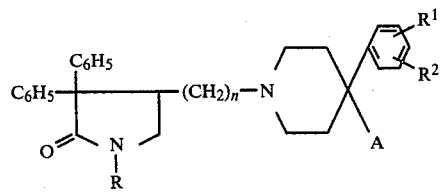

wherein R is hydrogen, lower alkyl, cyclohexyl or benzyl, $R^1$ is hydrogen, chloro, bromo, fluoro, trifluoromethyl or lower alkoxy, $R^2$ is hydrogen, chloro, bromo, or fluoro, A is hydroxy, lower-alkylcarbonyloxy or lower-alkoxycarbonyl and n is 1, 2 or 3 having analgetic and antidiarrheal activity are disclosed. The pharmaceutically acceptable acid addition salts of the bases are within the scope of the present invention.

6 Claims, No Drawings

HETEROCYCLIC ANTIDIARRHEAL COMPOSITIONS & METHODS OF USE

This application is a continuation-in-part of copending application Ser. No. 796,264 filed May 12, 1977, now U.S. Pat. No. 4,120,969, issued Oct. 17, 1978 which is a continuation-in-part of then copending application Ser. No. 615,952 filed Sept. 23, 1975, now abandoned, which is a continuation-in-part of then copending application Ser. No. 541,684 filed Jan. 16, 1975, also now abandoned.

The present invention relates to certain heterocyclic organic compounds which may be referred to as 4-(omega-substituted alkyl)-2-pyrrolidinones and is more particularly concerned with 1-R-4-(omega-substituted alkyl)-3,3-diphenyl-2-pyrrolidinones, processes for the production thereof, compositions containing the same as active ingredients, and the methods of making and using them.

The invention is especially concerned with compounds of the formula:

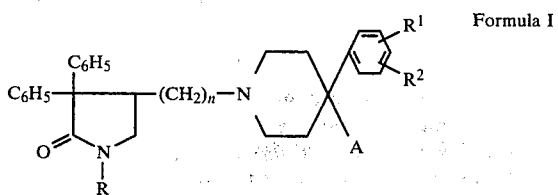

Formula I wherein:
R is hydrogen, lower alkyl, cyclohexyl or benzyl,
$R^1$ is hydrogen, chloro, bromo, fluoro, trifluoromethyl or lower alkoxy,
$R^2$ is hydrogen, chloro, bromo or fluoro,
A is hydroxy, lower-alkylcarbonyloxy or loweralkoxy carbonyl, and p1 n is 1, 2 or 3.

The pharmaceutically acceptable acid addition salts of the compounds of Formula I are included as part of the present invention.

The compounds of the invention having the foregoing Formula I are generally characterized by important pharmacological activity indicative of their use in counteracting certain physiological abnormalities in an animal body. The compounds possess analgetic and antidiarrheal properties.

The 1-R-4-[omega-(4-hydroxy-4-phenylpiperidinyl)alkyl]-3,3-diphenyl-2-pyrrolidinones of Formula I-A

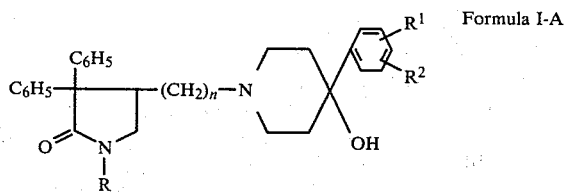

Formula I-A are included as part of the present invention as well as the pharmaceutically acceptable acid-addition salts thereof. The values of R, $R^1$, $R^2$ and n are as set forth hereinabove. The compounds of Formula I-A have anti-diarrheal properties.

It is, accordingly, an object of the present invention to provide novel and useful 1-R-4-(omega-substituted alkyl)-3,3-diphenyl-2-pyrrolidinones. A further object is to provide methods for the production of the novel 1-R-4-(omega-substituted alkyl)-3,3-diphenyl-2-pyrrolidinones. A still further object is to provide pharmaceutical compositions containing the novel compounds of the invention as active ingredients and methods for their use. Other objects of the invention will be apparent to one skilled in the art, and still other objects will become apparent hereinafter.

In the definitions of symbols in the foregoing Formula I and where they appear elsewhere throughout this specification, the terms have the following significance.

The term "lower-alkyl" as used herein includes straight and branched chain radicals of up to eight carbon atoms inclusive and is exemplified by such groups as methyl, ethyl, propyl, isopropyl, tertiary butyl, amyl, isoamyl, hexyl, heptyl, octyl, and the like. "Loweralkoxy" has the formula -O-lower-alkyl.

The invention also contemplates as mentioned hereinabove the pharmaceutically acceptable acid addition salts of the compounds of Formula I and I-A formed with non-toxic organic and inorganic acids. Such salts are easily prepared by methods known in the art. The acids which can be used to prepare the preferred non-toxic acid addition salts are those which produce, when combined with the free bases, salts whose anions are relatively innocuous to the animal organism in therapeutic doses of the salts, so that beneficial physiological properties inherent in the free bases are not vitiated by side effects ascribable to the anions.

The base is reacted with the calculated amount of organic or inorganic acid in aqueous miscible solvent, such as ethanol or isopropanol, with isolation of the salt by concentration and cooling, or the base is reacted with an excess of the acid in aqueous immiscible solvent, such as ethyl ether or isopropyl ether, with the desired salt separating directly. Exemplary of such organic salts are those formed with malaic, fumaric, benzoic, ascorbic, pamoic, succinic, methane sulfonic, citric, propionic, tartaric, citric, maleic acid, and the like.

Exemplary of such inorganic salts are those formed with hydrochloric, hydrobromic, sulfuric, sulfamic, phosphoric and nitric acids.

Generally speaking, the novel compounds of the present invention can be prepared according to the following reaction schemes. Hereinbelow R, $R^1$, $R^2$ and n are as defined in the generic formula and X is a halogen radical, chlorine being preferred.

(1) 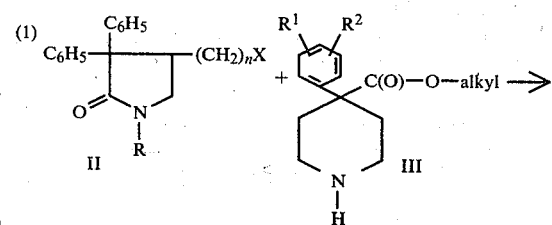

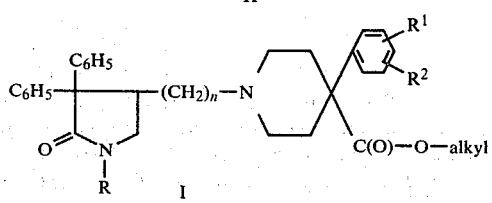

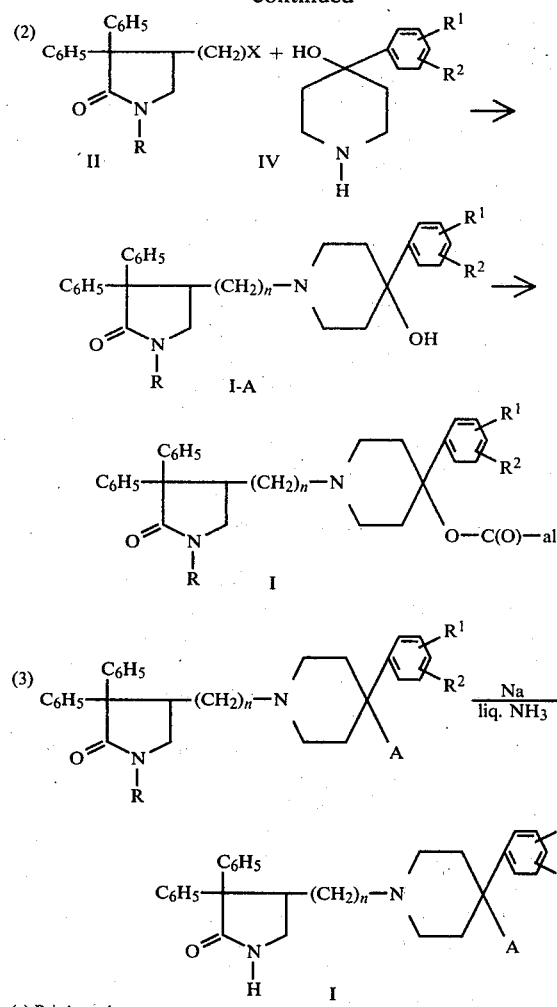

(a) R is benzyl

The 1-R-4-(omega-haloalkyl)-3,3-diphenyl-2-pyrrolidinones of Formula II wherein n is 2 or 3 are known compounds which are either disclosed or can be readily prepared by the procedures disclosed in U.S. Pat. No. 3,192,230.

The 1-R-4-(omega-haloalkyl)-3,3-diphenyl-2-pyrrolidinones of Formula II wherein n is 1 are novel compounds which are prepared by novel procedures disclosed in copending application Ser. No. 615,951 filed on even date herewith now U.S. Pat. No. 4,119,637, issued Oct. 10, 1978.

The novel compounds of Formula VI are prepared by the following procedure:

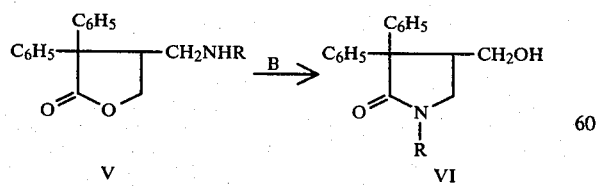

wherein R is as defined above and B is a basic catalyst.

According to the above procedure a 4,5-dihydro-3,3-diphenyl-4-hydrocarbylaminomethylfuran-2-(3H)one V is mixed with a catalytic amount of a strong base such as an alkali metal hydride, an alkali metal amide, an alkali metal tertiary butoxide or an alkali metal hydroxide, an alkali metal hydride being preferred, to cause intramolecular rearrangement to the 1-hydrocarbon-3,3-diphenyl-4-hydroxymethyl-2-pyrrolidinone VI. The novel intramolecular rearrangement is usually carried out with the application of heat, e.g., in refluxing isooctane, benzene, toluene, or like solvent, for an extended period, e.g., of from about 10 to about 20 hours. The pyrrolidinone generally separates from the cooled reaction mixture as a crystalline solid which is isolated by filtration and is further purified by crystallization from a suitable solvent or solvents.

The novel compounds of Formula V are prepared by the following procedure:

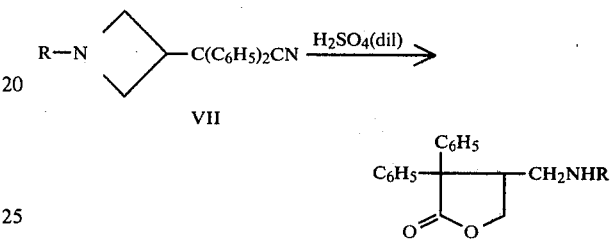

wherein R is as defined above.

According to the above procedure an α,α-diphenyl-α-(1-hydrocarbon-3-azetidinyl)acetonitrile is reacted with dilute sulfuric acid resulting in the formation of the 4,5-dihydrofuran-2-(3H)one ring. The novel reaction is usually carried out with the application of heat, e.g., at a temperature of from about 110° C. to about 140° C. for an extended period, e.g., of from about 35 hours to about 60 hours to effect the formation of the 4,5-dihydro-3,3-diphenyl-4-hydrocarbylaminomethylfuran-2(3H)one II from the α,α-diphenyl-α-(1-hydrocarbon-3-azetidinyl)acetonitrile. The product can be obtained from the reaction mixture by various methods but is preferably isolated by pouring the acidic reaction mixture onto ice, separation of the aqueous-organic layers, acid-base extraction of the organic layer and recrystallization of the 4,5-dihydrofuran-2(3H)one product from a suitable solvent.

The α,α-diphenyl-α-(1-hydrocarbon-3-azetidinyl)acetonitriles VII are prepared from 1-hydrocarbon-3-azetidinols by the following procedure:

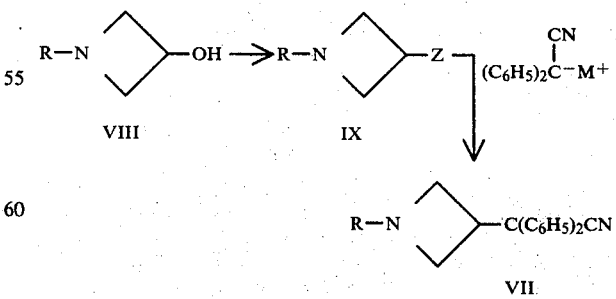

wherein R is as defined hereinabove, Z is a lower alkylsulfonyloxy radical, an arylsulfonyloxy radical or a halide radical, preferably chloride, and M+ is an alkali metal cation, preferably sodium or potassium.

According to the above procedure an alkyl or aryl sulfonate ester IX, or an azetidinyl halide IX, is prepared by methods known to the art. The alkali metal salt of diphenylacetontrile is prepared in a similar solvent by reacting diphenylacetonitrile with an alkali metal hydride or an alkali metal amide. The sodium and potassium metal hydrides and amides are preferred. The solution of the alkyl or aryl sulfonate ester or the azetidinyl halide is then reacted with the alkali metal salt of diphenylacetonitrile at an elevated temperature, preferably at the reflux temperature of the organic solvent used. The α,α-diphenyl-α-(1-hydrocarbon-3-azetidinyl)acetonitrile III thusly prepared is isolated from the reaction mixture by known procedures and further purified by crystallization from a suitable solvent or solvents.

The 1-hydrocarbon-3-azetidinols are known compounds or they can be prepared as described by V. R. Gaertner, Tetrahedron Letters No. 39, pp. 4691–4 (1966), by Okutani et al., Chem. Pharm. Bull. 22 (7) 1490–7 (1974), or by procedures disclosed in U.S. Pat. No. 3,668,196.

The 1-hydrocarbon-3,3-diphenyl-4-halomethyl-2-pyrrolidinones of Formula II

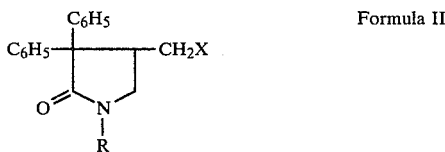

Formula II wherein R is as defined above and X is chloro, bromo or iodo are novel compounds and are readily prepared from the precursor hydroxy compounds. Thus, a 4-bromomethyl-3,3-diphenyl-1-isopropyl-2-pyrrolidinone can be prepared according to the procedure of Example 5 by substituting thionyl bromide for thionyl chloride. The 4-iodomethyl compound can be prepared by reacting a 4-chloromethyl compound with sodium iodide in acetone.

The 4-phenyl-4-lower-alkoxycarbonylpiperidine reactants of Formula III and the 4-hydroxy-4-phenyl-piperidine reactants of Formula IV and the substituted phenyl analogs thereof, e.g., 4-(p-fluorophenyl)-4-lower-alkoxycarbonylpiperidine, 4-hydroxy-4-(p-fluorophenyl)piperidine, 4-hydroxy-4-(m-trifluoromethylphenyl)piperidine and 4-hydroxy-4-(p-methoxyphenyl)-piperidine are either known compounds or they can be readily prepared by methods known to the art.

Thus, suitable piperidine compounds of Formula III and IV which can be used in the present invention include:
4-(p-fluorophenyl)-4-ethoxycarbonylpiperidine,
4-(p-bromophenyl)-4-ethoxycarbonylpiperidine,
4-(p-methoxyphenyl)-4-propoxycarbonylpiperidine,
4-(p-chlorophenyl)-4-propoxycarbonylpiperidine,
4-(m-trifluoromethylphenyl)-4-methoxycarbonylpiperidine,
4-(m-trifluoromethyl-p-chloro)-4-ethoxycarbonylpiperidine,
4-(m-trifluoromethyl-p-bromo)-4-ethoxycarbonylpiperidine,
4-hydroxy-4-(m-trifluoromethylphenyl)piperidine,
4-hydroxy-4-(m-trifluoromethyl-p-chlorophenyl)piperidine,
4-hydroxy-4-(p-chlorophenyl)piperidine,
4-hydroxy-4-(p-fluorophenyl)piperidine, and
4-hydroxy-4-(m-trifluoromethyl-p-fluoro)piperidine.

In a general method of preparation according to reaction sequence (I) a 1-R-4-(omega-haloalkyl)-3,3-diphenyl-2-pyrrolidinone (II) wherein n is 2 or 3, e.g., a 1-R-4-(2-chloroethyl)-3,3-diphenyl-2-pyrrolidinone or a 1-R-4-(3-chloropropyl)-3,3-diphenyl-2-pyrrolidinone and a 4-phenyl-4-lower-alkoxy-carbonylpiperidine (III) are reacted together in a lower alkanol solvent as, for example, n-butanol containing an acid binding agent such as a metal carbonate. The reaction is preferably run at reflux for a period of from about 12 hours to about 24 hours. The cooled reaction mixture is filtered, concentrated at reduced pressure, and the residual basic oil converted to a suitable acid addition salt which can be further purified by crystallization from a suitable solvent.

In reaction sequence (2) the reaction between a 1-R-4-(omega-haloalkyl)-3,3-diphenyl-2-pyrrolidinone (II) wherein n is 2 or 3, e.g., a 1-R-4-(2-chloroethyl)-3,3-diphenyl-2-pyrrolidinone or a 1-R-4-(3-chloropropyl)-3,3-diphenyl-2-pyrrolidinone and 4-hydroxy-4-phenyl-piperidine (IV) is carried out under the reaction conditions described hereinabove. The 1-R-4-[omega-(4-hydroxy-4-phenyl-1-piperidinyl)alkyl]-3,3-diphenyl-2-pyrrolidinone (V) is reacted with a lower-alkylcarbonyl chloride in a mixture of a chlorinated hydrocarbon, e.g., chloroform and ice water together with an acid binding agent such as a metal carbonate. The reaction is generally completed in a short time, the layers separated and the basic product isolated from the dried organic layer by concentration at reduced pressure. The basic material is converted to a suitable acid addition salt which can be further purified by crystallization from a suitable solvent.

When reaction sequence (I) or (II) is carried out using a compound of Formula II wherein n is 1, e.g., a 1-R-4-chloromethyl-3,3-diphenyl-2-pyrrolidinone, it is necessary to heat the reactants in a steel bomb at an elevated temperature of from about 180° C. to about 220° C. and for a period of from about 40 hours to about 60 hours to effect reaction between the 2-pyrrolidinone compound II and the piperidine reactants III and IV.

In reaction sequence (3) a 1-benzyl-4-[omega-(4-phenyl-4-A-piperidinyl)alkyl]-3,3-diphenyl-2-pyrrolidinone is debenzylated in liquid ammonia using sodium metal to furnish a compound of Formula I wherein R is hydrogen.

Another aspect of the present invention contemplates and provides a pharmaceutical preparation in dosage unit form adapted for administration to obtain an analgetic effect comprising per dosage unit, an analgetic effective, non-toxic amount within the range of from about 5 to about 100 milligrams of at least one compound of Formula I as defined hereinabove, and a pharmaceutical diluent.

A further aspect of the present invention contemplates and provides a pharmaceutical preparation in dosage unit form as described immediately hereinabove to obtain an antidiarrheal effect.

PREPARATION 1

α,α-Diphenyl-α-(1-isopropyl-3-azetidinyl)acetonitrile

A mixture of 168 g. (0.87 mole) of diphenylacetonitrile and 40.42 g. (0.96 mole) of 57% sodium hydride in one liter of dry toluene was stirred at reflux temperature for three hours.

A stirred solution of 1-isopropyl-3-azetidinol (100 g., 0.87 mole) and 101 g. (1.0 mole) of triethylamine in 300 ml. of dry benzene was treated dropwise with 100 g. (0.87 mole) of methylsulfonyl chloride and after stirring for two hours at room temperature the mixture was filtered and the filter cake was washed with dry benzene.

The benzene solution of 1-isopropyl-3-azetidinylmethane sulfonate was added dropwise to the stirred refluxing toluene mixture containing the sodium salt of diphenylacetonitrile and refluxing continued for 1.5 hours after addition. The cooled reaction mixture was treated with water, the layers separated, and the organic layer extracted with dilute hydrochloric acid and water. The combined extracts were basified using dilute sodium hydroxide and the base insoluble material extracted with chloroform. The dried extract was concentrated and the residual material was recrystallized from isooctane. The α,α-diphenyl-α-(1-isopropyl-3-azetidinyl)acetonitrile weighed 142 g. (55%) and melted at 93°-95° C.

Analysis: Calcd. for $C_{20}H_{22}N_2$: C,82.72; H,7.64; N,9.65; Found: C,82.72; H,7.73; N,9.55.

PREPARATION 2

α,α-Diphenyl-α-(1-methyl-3-azetidinyl)acetonitrile

A mixture of 4.0 g (0.11 mole) of sodium amide, 21 g. (0.11 mole) of diphenylacetonitrile and 300 ml. of toluene was stirred at reflux for 4 hours in a nitrogen atmosphere. The heat was removed and an equimolar amount of 3-chloro-1-methylazetidine in toluene was added at a rate which maintained refluxing. The reaction mixture was refluxed an additional 4 hours, allowed to stand overnight at room temperature, washed with water and extracted with dilute hydrochloric acid. The aqueous acid extract was made basic with dilute sodium hydroxide, the base insoluble oil extracted with isopropyl ether, the ether extract dried over sodium sulfate and concentrated. The residual solid was recrystallized from ligroin to give 6.7 g. (27%) of product, m.p. 113°-115° C.

Analysis: Calcd. for $C_{18}H_{18}N_2$: C,82.41; H,6.92; N,10.68; Found: C,82.31; H,6.98; N,10.51.

PREPARATION 3

α-(1-Cyclohexyl-3-azetidinyl)-α,α-diphenylacetonitrile

To 191 g. (1.0 mole) of 1-cyclohexyl-3-azetidinol hydrochloride in methylene chloride was added a dilute sodium hydroxide solution, the organic layer was extracted, dried (sodium sulfate), filtered and concentrated in vacuo. The residue was dissolved in dry benzene and stirred with 116 g. (1.05 mole) of triethylamine and cooled with an ice bath. One mole (115 g.) of methanesulfonylchloride was added, dropwise, and stirring was continued at room temperature for three hours and the mixture was filtered. The filtrate was added at a fast dropwise rate to a reaction mixture of 50.0 g. (1 mole) of sodium hydride in one liter of dry toluene to which 193 g. (1 mole) of diphenylacetonitrile had been added slowly at 45°-50° C. and had already stirred at reflux for two hours. After addition was complete, reflux was continued for two hours, and the solution was stirred overnight. An equivalent amount of isooctane was added, and after extracting four times with a dilute hydrochloric acid solution, the acid layers were combined and made basic with 50% sodium hydroxide, with ice cooling, and extracted with chloroform. The organic layer was dried, filtered and concentrated in vacuo. The solid which formed when the residue was treated with isopropyl ether was recrystallized from isopropyl ether twice. The product weighed 58.0 g. (18% yield) and melted at 111°-114° C.

Analysis: Calculated for $C_{23}H_{26}N_2$: C,83.59; H,7.93; N,8.48; Found: C,83.24; H,7.94; N,8.27.

PREPARATION 4

α,α-Diphenyl-α-[1-(1-phenylethyl-3-azetidinyl)-]acetonitrile

To a solution of 67.9 g. (0.67 mole) of triethylamine and 114 g. (0.64 mole) of 1-(1-phenylethyl)-3-azetidinol in 800 ml. of dry benzene was added dropwise 73.6 g. (0.65 mole) of methane sulfonyl chloride while cooling with an ice bath. After stirring for 2 hours at room temperature the mixture was filtered. Over a period of 40 minutes the filtrate was added dropwise to a refluxing suspension of the sodium salt of diphenyl acetonitrile prepared by refluxing 123.5 g. (0.64 mole) of the nitrile and 28.2 g. (0.7 mole) of 57% sodium hydride in one liter of dry toluene for 2.5 hrs. The resulting solution was refluxed for 2 hrs. and extracted with water. The toluene solution was extracted with dilute hydrochloric acid. Very little of the desired product went into the aqueous layer. The toluene was treated with water, followed by a volume of isooctane equal to the toluene causing an oil layer to form which was separated with the water layer. The toluene was washed several times and all aqueous layers combined. The aqueous-oil mixture was made basic with dilute sodium hydroxide and extracted with chloroform, which was dried (sodium sulfate) and concentrated. The residue was recrystallized from isooctane-isopropyl ether to give 94 g. (42%) of product melting at 122°-130° C. A 10 g. sample was recrystallized from the same solvent to give 7.8 g. of product melting at 130°-132° c.

Analysis: Calculated for $C_{25}H_{24}N_2$: C,85.19; H,6.86; N,7.95; Found: C,84.98; H,6.84; N,7.83.

PREPARATION 5

In the manner of the preceding discussion and in accordance with Preparations 1–4 starting with the appropriate 1-hydrocarbon-3-azetidinol and diphenylacetonitrile, the following α,α-diphenyl-α-(1-hydrocarbon-3-azetidinyl)acetonitriles are produced:

α,α-diphenyl-α-(1-ethyl-3-azetidinyl)acetonitrile from 1-ethyl-3-azetidinol and diphenylacetonitrile;

α,α-diphenyl-α-(1-propyl-3-azetidinyl)acetonitrile from 1-propyl-3-azetidinol and diphenylacetonitrile;

α,α-diphenyl-α-(1-butyl-3-azetidinyl)acetonitrile from 1-butyl-3-azetidinol and diphenylacetonitrile;

α,α-diphenyl-α-(1-isobutyl-3-azetidinyl)acetonitrile from 1-isobutyl-3-azetidinol and diphenylacetonitrile;

α,α-diphenyl-α-(1-benzyl-3-azetidinyl)acetonitrile from 1-benzyl-3-acetidinol and diphenylacetonitrile; and α,α-diphenyl-α-(1-phenethyl-3-azetidinyl)acetonitrile from 1-phenethyl-3-azetidinol and diphenylacetonitrile.

PREPARATION 6

4,5-Dihydro-3,3-diphenyl-4-isopropylaminomethylfuran-2-(3H)one

α,α-Diphenyl-α-(1-isopropyl-3-azetidinyl)acetonitrile (142 g.; 0.49 mole) was added to 500 g. of 70% sulfuric acid at 90°-100° C. The temperature was raised to 130° C. for 48 hours. The cooled mixture was poured onto ice and the cold mixture made basic ty the addition of solid sodium hydroxide. The basic mixture was extracted with chloroform and the combined chloroform extracts dried over sodium sulfate and concentrated. The residual material was crystallized from an 80% isooctane-20% isopropyl ether solution. The 4,5-dihydro-3,3-diphenyl-4-isopropylaminomethylfuran-2(3H)one weighed 105 g. (69.3%) and melted at 78°–80° C.

Analysis: Calcd. for $C_{20}H_{23}NO_2$: C,77.64; H,7.49; N,4.53; Found: C,77.68; H,7.36; N,4.23.

PREPARATION 7

4,5-Dihydro-3,3-diphenyl-4-methylaminomethylfuran-2-(3H)one Maleate

Sixty-four grams (0.24 mole) of α,α-diphenyl-α-(1-methyl-3-azetidinyl)acetonitrile was dissolved in 300 g. of 70% sulfuric acid solution at 110°–120° C. The solution was heated to 130° C. for 48 hours, poured onto ice, and made basic with the addition of sodium hydroxide while continuing to cool by adding ice. The mixture was extracted with chloroform, the combined extracts dried, filtered, and concentrated in vacuo. The residual oil was dissolved in isopropanol and treated with 28.0 g. of maleic acid. The maleate salt was recrystallized from ethanol-dimethylformamide. The dried maleate salt weighed 58.0 g. and melted at 189°–192° C.

Analysis: Calcd. for $C_{22}H_{23}NO_6$: C,66.49; H,5.83; N,3.53; Found: C,65.97; H,5.90; N,3.79.

PREPARATION 8

4,5-Dihydro-4-cyclohexylaminomethyl-3,3-diphenylfuran-2(3H)one

To 41.0 g. (0.12 mole) of α-(1-cyclohexyl-3-azetidinyl)-α,α-diphenylacetonitrile was added 100 g. of a 70% solution of sulfuric acid, and the mixture was stirred and heated at 120° C. for 48 hrs. The solution was then poured over ice and made basic with 50% sodium hydroxide, and extracted with chloroform. The organic layer was dried, filtered, and concentrated in vacuo. The residue was crystallized twice from isopropyl ether, the crystallized material weighed 8.0 g. (20% yield) and melted at 129°–131° C.

Analysis: Calculated for $C_{23}H_{27}NO_2$: C,79.05; H,7.79; N,4.01; Found: C,78.80; H,7.80; N,3.91.

PREPARATION 9

4,5-Dihydro-3,3-diphenyl-4-(1-phenylethylaminomethyl)furan-2(3H)one Maleate 4,5-Dihydrate-3,3-diphenyl-4-(1-phenylethylaminomethyl)furan-2(3H)one was prepared following the procedures described in the previous examples from α-[1-(1-phenylethyl-3-azetidinyl)]-α,α-diphenylacetonitrile. The maleate salt melting at 190°–192° C. was prepared from the free base.

PREPARATION 10

In the manner of the preceding discussion and in accordance with Preparations 11–13 starting with the appropriate α,α-diphenyl-α-(1-hydrocarbon-3-azetidinyl)acetonitrile and dilute sulfuric acid, the following 4,5-dihydro-3,3-diphenyl-4-hydrocarbylaminomethylfuran-2-(3H)ones are produced:

4,5-dihydro-3,3-diphenyl-4-ethylaminomethylfuran-2-(3H)one from α,α-diphenyl-α-(1-ethyl-3-azetidinyl)acetonitrile and dilute sulfuric acid;

4,5-dihydro-3,3-diphenyl-4-propylaminomethylfuran-2-(3H)one from α,α-diphenyl-α-(1-propyl-3-azetidinyl)acetonitrile and dilute sulfuric acid;

4,5-dihydro-3,3-diphenyl-4-isobutylaminomethylfuran-2-(3H)one from α,α-diphenyl-α-(1-isobutyl-3-azetidinyl)acetonitrile and dilute sulfuric acid;

4,5-dihydro-3,3-diphenyl-4-benzylaminomethylfuran-2-(3H)one from α,α-diphenyl-α-(1-benzyl-3-azetidinyl)acetonitrile and dilute sulfuric acid; and 4,5-dihydro-3,3-diphenyl-4-phenethylaminomethylfuran-2-(3H)one from α,α-diphenyl-α-(1-phenethyl-3-azetidinyl)acetonitrile and dilute sulfuric acid.

PREPARATION 11

3,3-Diphenyl-4-hydroxymethyl-1-isopropyl-2-pyrrolidinone

Fifty-three grams (0.17 mole) of 4,5-dihydro-3,3-diphenyl-4-isopropylaminomethylfuran-2-(3H)one was dissolved in 300 ml. of boiling isooctane and 0.25 g. of 67% sodium hydride added. After refluxing for 6.5 hours an additional 0.25 g. of 57% sodium hydride was added and refluxing was continued overnight. The cooled mixture was filtered and the solid was recrystallized from toluene. The 3,3-diphenyl-4-hydroxymethyl-1-isopropyl-2-pyrrolidinone weighed 42 g. (80%) and melted at 159°–161° C.

Analysis: Calcd. for $C_{20}H_{23}NO_2$: C,77.64; H,7.49; N,4.53; Found: C,77.71; H,7.52; N,4.37.

PREPARATION 12

1-Cyclohexyl-4-hydroxymethyl-3,3-diphenyl-2-pyrrolidinone

To 90.0 g. (0.26 mole) of 4-cyclohexylaminomethyl-4,5-dihydro-3,3-diphenylfuran-2-(3H)one in 500 ml. of isooctane was added 1.0 g. of sodium hydride (57% in mineral oil) as a catalyst and the mixture was refluxed overnight. Upon cooling a solid precipitated and the isooctane was decanted from the solid. The solid was recrystallized from isopropyl alcohol, weighed 66.0 g. (73% yield) and melted at 148°–150° C.

Analysis: Calcd. for $C_{23}H_{27}NO_2$: C,79.05; H,7.79; N,4.01; Found: C,78.97; H,7.74; N,3.92.

PREPARATION 13

4-Hydroxymethyl-3,3-diphenyl-1-(1-phenylethyl)-2-pyrrolidinone

Two hundred grams of 4,5-dihydro-4-(1-phenylethylaminomethyl)-3,3-diphenylfuran-2(3H)one maleate was partitioned between isopropyl ether and a dilute sodium hydroxide solution, the ether layer dried, filtered and concentrated in vacuo. Fifty grams (0.13 mole) of the residue was dissolved in hot isooctane with 1 g. of sodium hydride (50% in mineral oil) as a catalyst and refluxed overnight. The isooctane was decanted from the cooled liquid-solid mixture and the residue was recrystallized from a 90:10 mixture of isopropyl ether-:isopropanol. The solid weighed 34.0 g. (70% yield) and melted at 130°–144° C.

Analysis: Calcd. for $C_{25}H_{25}NO_2$: C,80.83; H,6.78; N,3.77; Found: C,80.80; H,6.85; N,3.66.

PREPARATION 14

4-Hydroxymethyl-1-methyl-3,3-diphenyl-2-pyrrolidinone

Forty grams (0.153 mole) of α,α-diphenyl-α-(1-methyl-3-azetidinyl)acetonitrile was heated in 150 g. of 70% sulfuric acid solution for 48 hrs. at 130° C. The reaction mixture was poured onto ice and made basic with a 50% sodium hydroxide solution while cooling with the addition of more ice. This mixture was extracted with chloroform, combined extracts dried, filtered, and concentrated in vacuo. The residue was crystallized from toluene, weighed 34.5 g. and melted at 148°–150° C. Ten grams was recrystallized twice from toluene, weighed 7.5 g., and melted at 149°–151° C.

Analysis: Calcd. for $C_{18}H_{19}NO_2$: C,76.84; H,6.81; N,4.98; Found: C,76.81; H,6.81; N,4.93.

PREPARATION 15

4-(Hydroxymethyl)-3,3-diphenyl-2-pyrrolidinone

To 750 ml. of methanol and 80.0 g. (0.22 mole) of 4-(1-phenylethylaminomethyl)-4,5-dihydro-3,3-diphenylfuran-2(3H)one was added 3.0 g. of palladium hydroxide catalyst and the mixture was shaken in three atmospheres of hydrogen at 70° C. for 18 hrs. Upon filtering starting material was found to be present; fresh catalyst was added to the solution which was shaken in three atmospheres of hydrogen at 70° C. for three more hours. After filtering the filtrate was concentrated in vacuo. The residue was dissolved in 100 ml. of ethyl acetate, and 100 ml. of isopropyl ether was added. A portion of the crystallized material was recrystallized from the same solvent system to give product melting at 145°–148° C.

Analysis: Calcd. for $C_{17}H_{17}NO_2$: C,76.38; H,6.41; H,5.24; Found: C,76.22; H,6.49; N,5.17.

PREPARATION 16

In the manner of the preceding discussion and in accordance with Preparations 11–13 starting with the appropriate 4,5-dihydro 3,3-diphenyl-4-hydrocarbylaminomethylfuran-2-(3H)one and sodium hydride, the following 3,3-diphenyl-4-hydroxymethyl-1-hydrocarbon-2-pyrrolidinones are produced:

3,3-diphenyl-4-hydroxymethyl-1-ethyl-2-pyrrolidinone from 4,5-dihydro-3,3-diphenyl-4-ethylaminomethylfuran-2(3H)one and sodium hydride;

3,3-diphenyl-4-hydroxymethyl-1-propyl-2-pyrrolidinone from 4,5-dihydro-3,3-diphenyl-4-propylaminomethylfuran-2-(3H)one and sodium hydride;

3,3-diphenyl-4-hydroxymethyl-1-butyl-2-pyrrolidinone from 4,5-dihydro-3,3-diphenyl-4-butylaminomethylfuran-2-(3H)one and sodium hydride;

3,3-diphenyl-4-hydroxymethyl-1-isobutyl-2-pyrrolidinone from 4,5-dihydro-3,3-diphenyl-4-isobutylaminomethylfuran-2-(3H)one and sodium hydride;

3,3-diphenyl-4-hydroxymethyl-1-benzyl-2-pyrrolidinone from 4,5-dihydro-3,3-diphenyl-4-benzylaminomethylfuran-2-(3H)one and sodium hydride, and 3,3-diphenyl-4-hydroxymethyl-1-phenethyl-2-pyrrolidinone from 4,5-dihydro-3,3-diphenyl-4-phenethylaminomethylfuran-2-(3H)one and sodium hydride.

PREPARATION 17

4-Chloromethyl-3,3-diphenyl-1-isopropyl-2-pyrrolidinone

A solution of 43 g. (0.14 mole) of 3,3-diphenyl-4-hydroxymethyl-1-isopropyl-2-pyrrolidinone in 250 ml. of chloroform was treated with 33 g. (0.28 mole) of thionyl chloride over a one minute period followed by the dropwise addition of 22 g. (0.23 mole) of pyridine over a 30 minute period. The mixture was refluxed 18 hours and then poured onto ice. The cold mixture was made basic by the addition of sodium hydroxide. The chloroform layer was separated, dried over sodium sulfate and concentrated. The residue was crystallized using charcoal from a 25% ethyl acetate—75% isopropyl ether mixture. The crystalline solid was recrystallized from a 75% ethanol—25% water mixture and then from isopropyl ether. The dried 4-chloromethyl-3,3-diphenyl-1-isopropyl-2-pyrrolidinone weighed 23 g. and melted at 114°–116° C.

Analysis: Calcd. for $C_{20}H_{22}NOCl$: C,73.27; H,6.76; N,4.27; Found: C,73.30; H,6.82; N,4.22.

PREPARATION 18

4-Chloromethyl-1-methyl-3,3-diphenyl-2-pyrrolidinone

To 25.0 g. (0.09 mole) of 4-hydroxy-1-methyl-3,3-diphenyl-2-pyrrolidinone, in 200 ml. of chloroform was added 21.4 g. (0.18 mole) of thionyl chloride. With stirring and ice bath cooling, 18.0 g. (0.23 mole) of pyridine was added dropwise. The solution was refluxed for two hours. After concentrating in vacuo, the residue was dissolved in chloroform and washed successively with dilute hydrochloric acid solution and dilute sodium hydroxide. The chloroform solution was dried, filtered, and concentrated in vacuo. The solid residue was recrystallized from a 50:50 ethyl acetate-isopropyl ether mixture. It weighed 16.0 g. (59% yield) and melted at 120°–122° C.

Analysis: Calcd. for $C_{18}H_{18}ClNO$: C,72.11; H,6.05; N,4.67; Found: C,71.83; H,6.04; N,4.72.

PREPARATION 19

4-Chloromethyl-1-cyclohexyl-3,3-diphenyl-2-pyrrolidinone

To 60.0 g. (0.17 mole) of 1-cyclohexyl-4-hydroxymethyl-3,3-diphenyl-2-pyrrolidinone in 400 ml. of chloroform was added 48.0 g. (0.40 mole) of thionylchloride with stirring. To this solution was added dropwise with ice bath cooling 40 g. (0.52 mole) of dry pyridine and the solution was refluxed for two hours. After concentrating in vacuo the residue was dissolved in chloroform and washed successively with dilute hydrochloric acid solution and dilute sodium hydroxide solution. The chloroform solution was dried (sodium sulfate), filtered, and concentrated in vacuo. The residue was recrystallized from isopropyl ether and after drying weighed 34.5 g. (55% yield) and melted at 124°–126° C.

Analysis: Calculated for $C_{23}H_{26}ClNO$: C,75.09; H,7.12; N,3.81; Found: C,74.73; H,7.12; N,3.75.

PREPARATION 20

4-(Chloromethyl)-3,3-diphenyl-1-(1-phenylethyl)-2-pyrrolidinone

To 34.0 g. (0.09 mole) of 4-(hydroxymethyl)-3,3-diphenyl-1-(1-phenylethyl)-2-pyrrolidinone in 200 ml.

of chloroform was added 25.0 g. (0.20 mole) of thionyl chloride. To this solution with stirring and ice bath cooling was added dropwise, 20.0 g. (0.26 mole) of dry pyridine maintaining the reaction mixture at 25° C. The solution was refluxed for 1.5 hours, concentrated in vacuo and the residue was dissolved in chloroform. The solution was washed successively with dilute hydrochloric acid solution and dilute sodium hydroxide solution. The chloroform solution was dried, filtered, and concentrated in vacuo. The residue was dissolved in hot isopropyl ether and some isooctane was added. The hot solution was decanted from a gummy residue and the product crystallized from the cooled solution. Seven grams were recrystallized in isopropyl ether to give the product which melted at 115°–120° C.

Analysis: Calcd. for $C_{28}H_{24}ClNO$: C,77.01; H,6.20; N,3.59; Found: C,77.11; H,6.31; N,3.55.

PREPARATION 21

4-(Chloromethyl)-3,3-diphenyl-2-pyrrolidinone

To 30.0 g. (0.11 mole) of 4-(hydroxymethyl)-3,3-diphenyl-2-pyrrolidinone in 200 ml. of chloroform was added 25.0 g. (0.20 mole) of thionyl chloride. To this stirring solution was added dropwise with ice bath cooling 20.0 g. (0.26 mole) of dry pyridine maintaining room temperature. The solution was refluxed for 2.5 hours. Upon cooling, the chloroform solution was washed successively with dilute hydrochloric acid solution and dilute sodium hydroxide solution. The chloroform was dried, filtered and concentrated in vacuo. The solid residue was recrystallized twice from ethyl acetate-isopropanol to give product melting at 218°–219° C.

Analysis: Calcd. for $C_{17}H_{16}ClNO$: C, 71.45; H,5.64; N,4.90; Found: C,71.22; H,5.60; N,4.91.

EXAMPLE 1

1-Isopropyl-3,3-diphenyl-4-[2-(4-hydroxy-4-phenylpiperidinyl)ethyl]-2-pyrrolidinone Hydrochloride A stirred mixture of 26.5 g. (0.078 mole) of 4-(2-chloroethyl)-1-isopropyl-3,3-diphenyl-2-pyrrolidinone, 14 g. (0.078 mole) of 4-phenyl-4-piperidinol and 27 g. of potassium carbonate was refluxed for 18 hrs. The mixture was cooled, filtered and the filtrate was evaporated to an oil. The crude product was dissolved in ether and treated with ethereal hydrogen chloride. After recrystallization from isopropanol the product melted at 130°–132° C. (31.5 g.; 77%).

Analysis: Calculated for $C_{32}H_{39}ClN_2O_2$: C,74.03; H,7.57; N,5.40; Found: C,73.71; H,7.61; N,5.14.

EXAMPLE 2

1-Isopropyl-3,3-diphenyl-4-[2-(4-phenyl-4-propionoxypiperidinyl)ethyl]-2-pyrrolidinone Oxalate A stirred mixture of 0.04 mole of 4-[2-(4-hydroxy-4-phenyl-1-piperidinyl)ethyl]-1-isopropyl-3,3-diphenyl-2-pyrrolidinone and 60 g. of potassium carbonate in 50 ml. of chloroform was treated with 4.5 g. (0.05 mole) of propionyl chloride in 25 ml. of chloroform. After stirring for one hour the mixture was cooled to 0° in ice and treated with 100 ml. of crushed ice. The mixture was stirred until the ice melted, the chloroform layer was separated, dried over magnesium sulfate and evaporated to an oil. The oxalate salt was prepared in isopropanol and precipitated with isopropyl ether. Recrystallization from the same solvent system gave 14.5 g. (58%), m.p. 178°–180° C.

Analysis: Calculated for $C_{37}H_{44}N_2O_7$: C,70.68; H,7.05; N,4.45; Found: C,70.47; H,6.82; N,4.66.

EXAMPLE 3

1-Isopropyl-3,3-diphenyl-4-[2-phenyl-4-ethoxycarbonylpiperidinyl)ethyl]-2-pyrrolidinone Oxalate A stirred mixture of 15 g. (0.044 mole) of 4-(2-chloroethyl)-1-isopropyl-3,3-diphenyl-2-pyrrolidinone, 0.044 mole of 4-ethoxycarbonyl-4-phenylpiperidine and 15 g. of potassium carbonate in 50 ml. of n-butanol was refluxed for 24 hours. The mixture was cooled, filtered and evaporated to an oil. An oxalate salt was prepared in isopropanol and precipitated with isopropyl ether. The white salt was amorphous and solvated but gave a good analysis after drying at 110° C. under vacuum. The compound melted over a wide range below 100° C. The dried salt weighed 22.5 g. (80%).

Analysis: Calculated for $C_{37}H_{44}N_2O_7$: C,70.68; H,7.05; N,4.45; Found: C,70.45; H,6.94; N,4.34.

EXAMPLES 4–19

By following the manipulative procedures disclosed hereinabove and in the preceding examples and using the appropriately substituted 1-R-4-(omega-haloalkyl)-3,3-diphenyl-2-pyrrolidinone and 4-hydroxy-4-phenylpiperidines and 4-phenyl-4-lower-alkoxy-carbonylpiperidines, the following compounds are prepared:

1-methyl-4-{2-[4-(p-fluorophenyl)-4-ethoxycarbonylpiperidinyl]ethyl}-3,3-diphenyl-2-pyrrolidinone, 1-methyl-4-{2-[4-(p-bromophenyl)-4-ethoxycarbonylpiperidinyl]ethyl}-3,3-diphenyl-2-pyrrolidinone, 1-ethyl-4-{2-[4-(p-methoxyphenyl)-4-propoxycarbonyl piperidinyl]ethyl}-3,3-diphenyl-2-pyrrolidinone, 1-isopropyl-4-{2-[4-(p-chlorophenyl)-4-propoxycarbonyl piperidinyl]ethyl}-3,3-diphenyl-2-pyrrolidinone, 1-isopropyl-4-{2-[4-(m-trifluoromethylphenyl)-4-methoxy carbonylpiperidinyl]ethyl}-3,3-diphenyl-2-pyrrolidinone, 1-propyl-4-{2-[4-(m-trifluoromethyl-p-chlorophenyl)-4-ethoxycarbonylpiperidinyl]ethyl}-3,3-diphenyl-2-pyrrolidinone, 1-methyl-4-{2-[4-(m-trifluoromethyl-p-bromophenyl)-4-ethoxycarbonylpiperidinyl]ethyl}-3,3-diphenyl-2-pyrrolidinone, 1-methyl-4-{2-[4-hydroxy-4-(m-trifluoromethylphenyl)piperidinyl]ethyl}-3,3-diphenyl-2-pyrrolidinone, 1-methyl-4-{3-[4-hydroxy-4-(m-trifluoromethylphenyl)piperidinyl]propyl}-3,3-diphenyl-2-pyrrolidinone, 1-ethyl-4-{2-[4-hydroxy-4-(m-trifluoromethyl-p-chlorophenyl)piperidinyl]ethyl}-3,3-diphenyl-2-pyrrolidinone, 1-ethyl-4-{2-[4-hydroxy-4-(p-chlorophenyl)piperidinyl]ethyl}-3,3-diphenyl-2-pyrrolidinone, 1-isopropyl-4-{3-[4-hydroxy-4-(p-fluorophenyl)piperidinyl]ethyl}-3,3-diphenyl-2-pyrrolidinone, 1-isopropyl-4-{3-[4-hydroxy-4-(m-trifluoromethyl-p-fluorophenyl)piperidinyl]propyl}-3,3-diphenyl-2-pyrrolidinone, 1-ethyl-4-{2-[4-propionoxy-4-(m-trifluoromethyl-p-chloro phenyl)piperidinyl]ethyl}-3,3-diphenyl-2-pyrrolidinone, 1-ethyl-4-{2-[4-propionoxy-4-(p-chlorophenyl)piperidinyl]ethyl}-3,3-diphenyl-2-pyrrolidinone, 1-isopropyl-4-{3-[4-propionoxy-4-(m-trifluoromethyl-p-chlorophenyl)piperidinyl]propyl}-3,3-diphenyl-2-pyrrolidinone.

1-benzyl-4-{2-[4-hydroxy-4-(m-trifluoromethylphenyl)-piperidinyl]ethyl}-3,3-diphenyl-2-pyrrolidinone, 1-benzyl-4-{3-[4-hydroxy-4-(p-fluorophenyl)-piperidinyl]propyl}-3,3-diphenyl-2-pyrrolidinone, 1-benzyl-4-{2-[4-propionoxy-4-(m-trifluoromethylphenyl)piperidinyl]ethyl}-3,3-diphenyl-2-pyrrolidinone, 1-benzyl-4-{3-[4-propionoxy-4-(p-fluorophenyl)-piperidinyl]propyl}-3,3-diphenyl-2-pyrrolidinone, 1-benzyl-4-{2-[4-(p-chlorophenyl)-4-propoxycarbonyl piperidinyl]ethyl}-3,3-diphenyl-2-pyrrolidinone, 4-{2-[4-propionoxy-4-(m-trifluoromethylphenyl)-piperidinyl]ethyl}-3,3-diphenyl-2-pyrrolidinone, 4-{3-[4-propionoxy-4-(p-fluorophenyl)piperidinyl]-propyl}-3,3-diphenyl-2-pyrrolidinone, 4-{2-[4-(p-chlorophenyl)-4-propoxycarbonylpiperidinyl]ethyl}-3,3-diphenyl-2-pyrrolidinone.

EXAMPLE 20

3,3-Diphenyl-1-isopropyl-4-(4-phenyl-4-hydroxypiperidinylmethyl)-2-pyrrolidinone Maleate A mixture of 15 g. (0.046 mole) of 4-chloromethyl-3,3-diphenyl-1-isopropyl-2-pyrrolidinone, 8.1 g. (0.046 mole) of 4-hydroxy-4-phenylpiperidine, 8.2 g. (0.06 mole) of potassium carbonate and 200 ml. of ethanol was heated in a steel bomb at 200° C. for 48 hours. The cooled mixture was partitioned between water and isopropyl ether. The dried isopropyl ether layer (sodium sulfate) was concentrated. The residual material (19 g.) was dissolved in 150 ml. of isopropyl alcohol to which solution was added 7.0 g of maleic acid and 50 ml. of isopropyl ether. The maleate salt was collected and recrystallized from isopropyl alcohol-water. The dried salt weighed 8.0 g and melted at 207°-208° C.

Analysis: Calcd. for $C_{35}H_{40}N_2O_6$: C, 71.90; H, 6.90; N, 4.79; Found: C, 72.19; H, 6.95; N, 4.72.

EXAMPLE 21

3,3-Diphenyl-1-isopropyl-4-(4-phenyl-4-propionoxypiperidinylmethyl)-2-pyrrolidinone Eight grams of 3,3-diphenyl-1-isopropyl-4-(4-phenyl-4-hydroxypiperidinylmethyl)-2-pyrrolidinone was dissolved in benzene, 0.58 g. of 57% sodium hydride was added and after two hours stirring at room temperature 1.56 g. of propionic anhydride was added. Partial reaction occurred after two hours reaction time. An additional 1.0 g. of 57% sodium hydride and 3.0 g. of propionic anhydride was added and the mixture stirred overnight at room temperature and then refluxed for 48 hours. The cooled mixture was washed with water, the benzene layer dried over sodium sulfate and concentrated. The residue was chromatographed on a magnesium silicate column and the product eluted from the column using benzene and increasing amounts of acetone. The product was isolated and confirmed by its nuclear magnetic resonance spectra.

EXAMPLE 22

1-Methyl-3,3-diphenyl-4-[(4-hydroxy-4-phenyl-1-piperidinyl)methyl]-2-pyrrolidinone Fumarate (3:4)

To 100 ml. of ethanol was added 10.0 g. (0.033 mole) of 4-chloromethyl-1-methyl-3,3-diphenyl-2-pyrrolidinone, 5.8 g. (0.033 mole) of 4-hydroxy-4-phenylpiperidine and 13.8 g. (0.10 mole) of potassium carbonate (finely ground). The mixture was heated in a steel bomb with stirring in an oven for 48 hours at 200° C. After concentrating in vacuo, the residue was partitioned between dilute sodium hydroxide solution and chloroform. The chloroform was dried, filtered and concentrated in vacuo. The residue was dissolved in isopropanol and treated with oxalic acid, and the starting piperidine compound was obtained as an oxalate. The filtrate was concentrated in vacuo, and the residue was partitioned between dilute hydrochloric acid and ethyl acetate. The acid solution was made basic with dilute sodium hydroxide and was extracted with chloroform. The chloroform solution was dried (sodium sulfate), filtered and concentrated in vacuo. The residue was dissolved in hot isopropyl ether and treated with an equivalent amount of fumaric acid dissolved in isopropanol. The resulting salt was recrystallized from ethanol. The salt was triturated with acetonitrile to remove ethanol in the form of a solvate and dried. The salt (2.5 g., 14%) melted at 202°-205° C.

Analysis: Calculated for $C_{32}H_{35}N_2O_5$: C, 72.84; H, 6.69; N, 5.31; Found: C, 72.95; H, 6.73; N, 5.33.

EXAMPLE 23

4-{[4-(4-Chlorophenyl)-4-hydroxy-1-piperidinyl]methyl}-1-methyl-3,3-diphenyl-2-pyrrolidinone Fumarate To a steel bomb was added 17.0 g. (0.057 mole) of 4-chloromethyl-1-methyl-3,3-diphenyl-2-pyrrolidinone in 150 ml. of ethanol, 12.0 g. (0.057 mole) of 4-(p-chlorophenyl)-4-hydroxypiperidine and 21.2 g. (0.17 mole) of finely ground potassium carbonate. The mixture was heated with stirring to 200° C. for 48 hours. After concentrating the mixture in vacuo, the residue was partitioned between dilute hydrochloric acid solution and isopropyl ether. The ether was discarded, the acid solution was made basic with 50 percent sodium hydroxide solution and the base insoluble material was extracted with chloroform. The chloroform was dried, filtered and concentrated in vacuo. The residue was dissolved in a mixture of isopropyl ether and isopropanol and treated with an equivalent of fumaric acid. The fumarate salt was recrystallized twice from ethanol and once from isopropanol-methanol. The fumarate salt (2.0 g., 10%) melted at 213°-215° C.

Analysis: Calcd for $C_{33}H_{35}ClN_2O_6$: C, 67.06; H, 5.97; N, 4.74; Found: C, 67.44; H, 5.93; N, 4.79.

EXAMPLE 24

1-Cyclohexyl-4-[(4-hydroxy-4-phenyl-1-piperidinyl)-methyl]-3,3-diphenyl-2-pyrrolidinone To 150 ml. of ethanol in a steel bomb was added 15.0 g. (0.041 mole) of 1-cyclohexyl-4-chloromethyl-3,3-diphenyl-2-pyrrolidinone, 7.23 g. (0.041 mole) of 4-hydroxy-4-phenyl piperidine and 17.0 g. (0.12 mole) of potassium carbonate. The bomb was heated in an oven at 200° C. with stirring for 48 hours. The mixture was concentrated in vacuo, and the residue was partitioned between dilute sodium hydroxide solution and chloroform. The chloroform layer was dried, filtered, and concentrated in vacuo. The residue was dissolved in ethyl acetate and treated with ethereal hydrogen chloride. The solid which precipitated was the hydrochloride of starting piperidine compound. A further precipitate from the filtrate of this material contained a by-product of the reaction. The by-product was separated by filtration and the filtrate concentrated. The residue was partitioned between chloroform and sodium hydroxide solution, and the chloroform, after drying, was concentrated in vacuo. The residue was placed on a magnesium silicate column using chloroform as the eluent. The product was obtained upon subsequent washings of one and two percent methanol in chloroform. The washings were concentrated in vacuo, and the residue crystallized using an isopropyl ether-ethyl acetate mixture. The solid (1.5 g.; m.p. 179°–184° C.) after recrystallizing from ethyl acetate weighed 1.0 g. and melted at 188°–190° C.

Analysis: Calculated for $C_{34}H_{40}N_2O_2$: C, 80.28; H, 7.93; N, 5.51; Found: C, 80.12; H, 7.86; N, 5.40.

EXAMPLE 25

4-[(4-Hydroxy-4-phenyl-1-piperidinyl)methyl]-3,3-diphenyl-2-pyrrolidinone Hydrochloride To 10.0 g. (0.035 mole) of 4-(chloromethyl)-3,3-diphenyl-2-pyrrolidinone in 150 ml. of ethanol in a steel bomb was added 15.0 g. (0.11 mole) of potassium carbonate (finely ground) and 6.2 g. (0.035 mole) of 4-hydroxyl-4-phenylpiperidine. The mixture was heated to 200° C. for 48 hours and rotated slowly to effect mild stirring. After concentrating in vacuo, the residue was partitioned between dilute hydrochloric acid solution and ethyl acetate. The acid solution was made basic with sodium hydroxide and extracted with chloroform. The chloroform was dried, filtered and concentrated in vacuo. The residue was dissolved in isopropanol and treated with oxalic acid, and the oxalate salt of the starting piperidine compound precipitated out. The filtrate was concentrated in vacuo and the residue was partitioned between dilute sodium hydroxide and chloroform. The chloroform solution was dried (sodium sulfate), filtered, and concentrated in vacuo. The residue was dissolved in ethyl acetate and a solid formed which was filtered off. The filtrate was treated with ethereal hydrogen chloride and the hydrochloride salt was recrystallized in isopropanol-methanol. The salt (2.6 g., 17%) melted above 250° C.

Analysis: Calculated for $C_{28}H_{31}ClN_2O_2$: C, 72.63; H, 6.75; N, 6.05; Found: C, 72.44; H, 6.69; N, 6.06.

EXAMPLE 26

4-{[4-(4-Chlorophenyl)-4-hydroxyl-1-piperidinyl]methyl}-3,3-diphenyl-1-(1-methylethyl)-2-pyrrolidinone Oxalate Monohydrate A mixture of 18 g. (0.06 mole) of 4-chloromethyl-1-(1-methylethyl)-3,3-diphenyl-2-pyrrolidinone, 11.6 g. (0.06 mole) of 4-(4-chlorophenyl)-4-hydroxypiperidine and 20 g. (0.14 mole) potassium carbonate in 200 ml. of ethanol was heated to 200° C. for 48 hrs. in a steel bomb. During the heating the bomb was continuously rotated to produce mild stirring. The mixture was concentrated and the residue partitioned between chloroform sodium hydroxide. The chloroform was dried (sodium sulfate) and concentrated. The residue was dissolved in ethylacetate and treated with ethereal hydrogen chloride. The mixture was filtered and the filtrate extracted with water. The acid layer was made basic with dilute sodium hydroxide and extracted with chloroform which was dried (sodium sulfate) and concentrated. The residue was dissolved in isopropyl alcohol and treated with oxalic acid. The resulting crystals were recrystallized from ethanol-water. The product (3 g., 10%) melted at 240° C. (dec.).

Analysis: Calculated for $C_{33}H_{39}ClN_2O_7$: C, 64.86; H, 6.43; N, 4.58; Found: C, 65.13; H, 6.21; N, 4.46.

EXAMPLE 27

4-{[4-(4-Chlorophenyl)-4-hydroxyl-1-piperidinyl]methyl}-1-cyclohexyl-3,3-diphenyl-2-pyrrolidinone A mixture of 39 g. (0.106 mole) of 4-chloromethyl-1-cyclohexyl-3,3-diphenyl-2-pyrrolidinone, 58.5 g. (0.424 mole) of finely ground potassium carbonate, and 22.5 g. (0.106 mole) of 4-(4-chlorophenyl)-4-hydroxypiperidine in 300 ml. of ethanol was heated to 200° C. in a steel bomb for 66 hrs. During the heating the bomb was continuously rotated to produce mild stirring. The contents were filtered and the filtrate concentrated. The residue was heated in 250 ml. of ethylacetate and allowed to stand at room temperature overnight. The mixture was filtered. The filtrate was extracted with dilute hydrochloric acid and dilute sodium hydroxide. The ethylacetate was concentrated and the residue dissolved in ethanol and allowed to stand overnight. The resulting mixture was filtered and the filtrate concentrated. The residue was chromatographed on a 4.5×60 cm. silica gel column. The product was obtained from the column using a chloroform-methanol eluate containing increasing amounts of methanol. The product after isolation and crystallization from isopropanol melted at 222°–225° C.

Analysis: Calculated for $C_{34}H_{39}ClN_2O_2$: C, 75.19; H, 7.24; N, 5.16; Found: C, 75.41; H, 7.28; N, 5.15.

The compounds of this invention of Formula I-A produce inhibition of diarrhea. The activity is demonstrated by administration to mice at doses of about 30 mg/kg. to about 100 mg/kg. orally compounds of Formula I-A. One hour post drug administration the mice are given 50 mg/kg. of 5-hydroxytryptophane intraperitoneally. Control animals are only given 5-hydroxytryptophane. Compounds which inhibit the peristalsis effect of 5-hydroxytryptophane are considered active anti-diarrheals.

The compounds of this invention of Formula I wherein A is lower-alkyl carbonyloxy or lower-alkoxy carbonyl produce analgesia in animals. The analgetic activity is demonstrated by administering the compounds to mice at 20 mg/kg. intraperitoneally.

Effective quantities of any of the foregoing pharmacologically active compounds of Formula I may be administered to a living animal body for therapeutic purposes according to usual modes of administration and in usual forms, such as orally, in solutions, emulsions, suspensions, pills, tablets and capsules, or intramuscularly or parenterally in the form of sterile solutions or suspensions, and intravenously, in some cases, also in sterile solutions.

Although very small quantities of the active materials of the present invention are effective when minor therapy is involved or in cases of administration to subjects having a relatively low body weight, unit dosages are usually from 5 milligrams or above and preferably 25, 50, or 100 milligrams or even higher, depending of course upon the emergency of the situation and the particular result desired. Five to 50 milligrams appears optimum per unit dose, or usual broader ranges appear to be 1 to 100 milligrams per unit dose. Daily dosages should preferably range from 10 mg. to 100 mg. It is only necessary that the active ingredient constitute an effective amount, i.e., such that a suitable effective dosage will be obtained consistent with the dosage form employed. Obviously, several unit dosage forms may be administered at about the same time.

The following formulations are representative for all of the pharmacologically active compounds of this invention.

FORMULATIONS (1) Capsules

Capsules of 10 mg., 25 mg., and 50 mg. of active ingredient per capsule are prepared. With the higher amounts of active ingredients, reduction may be made in the amount of lactose.

| Typical blend for encapsulation | Per capsule, mg. |
|---|---|
| Active ingredient, as salt | 10 |
| Lactose | 259 |
| Starch | 126 |
| Magnesium stearate | 4 |
| Total | 399 |

Additional capsule formulations preferably contain a higher dosage of active ingredient and are as follows:

| Ingredients | 100 mg. per Capsule | 250 mg. per Capsule | 500 mg. per Capsule |
|---|---|---|---|
| Active ingredient | 100 | 250 | 500 |
| Lactose | 214 | 163 | 95 |
| Starch | 87 | 81 | 47 |
| Magnesium stearate | 4 | 6 | 8 |
| Total | 405 | 500 | 650 |

In each case, uniformly blend the selected active ingredient with lactose, starch, and magnesium stearate and encapsulate the blend.

(2) Tablets

A typical formulation for a tablet containing 10.0 mg. of active ingredient per tablet follows. The formulation may be used for other strengths of active ingredient by adjustment of weight of dicalcium phosphate.

| | Per tablet, mg. |
|---|---|
| 1. Active ingredient | 10.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 206.0 |

Uniformly blend the active ingredient, lactose, and dicalcium phosphate. Granulate the blend with starch paste and pass the wet mass through an eight mesh screen. The wet granulation is dried and sized through a twelve mesh screen. The dried granules are blended with the calcium stearate and compressed.

Additional tablet formulations preferably contain a higher dosage of the active ingredients and are as follows:

| A. 50 mg. tablet Ingredients: | Per tablet, mg. |
|---|---|
| Active ingredient | 50.0 |
| Lactose | 100.0 |
| Milo starch | 50.0 |
| Corn starch | 50.0 |
| Calcium stearate | 2.0 |
| Total | 252.0 |

Uniformly blend the active ingredient, lactose, milo starch, and corn starch. This blend is granulated using water as a granulating medium. The wet granules are passed through an eight mesh screen and dried at 140 to 160 degrees Fahrenheit overnight. The dried granules are passed through a number ten mesh screen and blended with the proper amount of calcium stearate and this blend is then converted into tablets on a suitable tablet press.

| B. 100 mg. tablet Ingredients: | Per tablet, mg. |
|---|---|
| Active ingredient | 100.0 |
| Lactose | 90.0 |
| Dicalcium phosphate | 90.0 |
| Starch | 33.0 |
| Milo starch | 17.0 |
| Calcium stearate | 2.0 |
| Total | 332.0 |

Uniformly blend the active ingredient, lactose, dicalcium phosphate, starch and milo starch. This blend is granulated with water and the wet mass is passed through a number eight mesh screen. The wet granules are dried at 140–160 degrees Fahrenheit overnight. The dried granules are passed through a number ten mesh screen. These dried granules are blended with the proper weight of calcium stearate and the lubricated granules are then converted into tablets on a suitable tablet press.

| C. 250 mg. tablet Ingredients: | Per tablet, mg. |
|---|---|
| Active ingredient | 250.0 |
| Corn starch | 20.0 |
| Carbowax 6000 (polyethylene glycol of M.W. approx. 6000) | 10.0 |
| Lactose | 20.0 |
| Magnesium stearate | 2.0 |
| Total | 302.0 |

Uniformly blend the active ingredient, Carbowax 6000, lactose, and one-half the weight of magnesium stearate required. This blend is then "slugged" on a suitable tablet press. These "slugs" are granulated through a ten mesh screen on an oscillating granulator. These granules are then blended with the remainder of the magnesium stearate and the lubricated granules are then converted into tablets on a suitable tablet press.

| D. 500 mg. tablet Ingredients: | Per tablet, mg. |
|---|---|
| Active ingredient | 500.0 |
| Corn starch (wet) | 50.0 |
| Milo starch | 20.0 |
| Calcium stearate | 6.0 |
| Corn starch (dry) | 20.0 |
| Total | 596.0 |

Uniformly blend the active ingredient, corn starch and milo starch. This blend is wet granulated using water and the wet mass is passed through a number eight mesh screen. These wet granules are dried overnight at 140–160 degrees Fahrenheit. The dried granules are passed through a number ten mesh screen. The dried granules and calcium stearate are uniformly blended and these lubricated granules are compressed on a suitable tablet press.

(3) Injectable-2% sterile solution.

|  |  | Per cc. |
| --- | --- | --- |
| Active ingredient | mg. | 5.0 |
| Preservative, e.g., chlorobutanol, percent wt./vol. |  | 0.5 |
| Water for injection |  | q.s. |

Prepare solution, clarify by filtration, fill into vials, seal, and autoclave.

I claim:

1. A method for the treatment of a warm-blooded animal afflicted with diarrhea which comprises administering to said animal in an amount sufficient to relieve said diarrhea, a compound selected from the group consisting of 1-R-4-(omega-substituted alkyl)-3,3-diphenyl-2-pyrrolidinones of the formula:

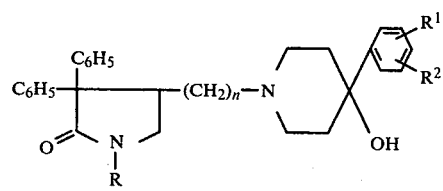

wherein;

R is selected from the group consisting of hydrogen, lower alkyl, cyclohexyl and benzyl, $R^1$ is selected from the group consisting of hydrogen, chloro, bromo, fluoro, trifluoromethyl and loweralkoxy, $R^2$ is selected from the group consisting of hydrogen, chloro, bromo and fluoro, and n is 1, 2 or 3 and the pharmaceutically acceptable acid addition salts thereof.

2. The method of claim 1 wherein the compound is 1-methyl-3,3-diphenyl-4-[(4-hydroxy-4-phenyl-1-piperidinyl)methyl]-2-pyrrolidinone.

3. The method of claim 1 wherein the compound is 1-methyl-3,3-diphenyl-4-[(4-hydroxy-4-phenyl-1-piperidinyl)methyl]-2-pyrrolidone fumarate (3:4).

4. An antidiarrheal composition comprising 1 to 500 mg. of a compound selected from the group consisting of 1-R-4-(omega-substituted alkyl)-3,3-diphenyl-2-pyrrolidinones of the formula:

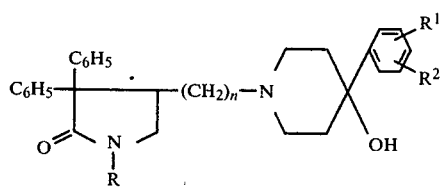

wherein;

R is selected from the group consisting of hydrogen, lower alkyl, cyclohexyl and benzyl, $R^1$ is selected from the group consisting of hydrogen, chloro, bromo, fluoro, trifluoromethyl and loweralkoxy, $R^2$ is selected from the group consisting of hydrogen, chloro, bromo, and fluoro, and n is 1, 2 or 3, and the pharmaceutically acceptable acid addition salts thereof in admixture with a pharmaceutically acceptable carrier.

5. The composition of claim 4 wherein the compound is 1-methyl-3,3-diphenyl-4-[(4-hydroxy-4-phenyl-1-piperidinyl)methyl]-2-pyrrolidinone.

6. The composition of claim 4 wherein the compound is 1-methyl-3,3-diphenyl-4-[(4-hydroxy-4-phenyl-1-piperidinyl)methyl]-2-pyrrolidinone fumarate (3:4).

* * * * *